United States Patent [19]
Salyer et al.

[11] Patent Number: 5,824,181
[45] Date of Patent: Oct. 20, 1998

[54] SURGICAL IMPLEMENT HANDLE MACHINE

[75] Inventors: Brian D. Salyer; John E. Hand, both of Warsaw, Ind.

[73] Assignee: Othy, Inc., Warsaw, Ind.

[21] Appl. No.: 588,993

[22] Filed: Jan. 19, 1996

[51] Int. Cl.$^6$ .......................... B32B 31/20; B23Q 15/00
[52] U.S. Cl. .................. 156/379.8; 156/293; 156/380.9; 29/714; 264/40.6; 425/143
[58] Field of Search .................... 29/714, 715; 264/40.6, 264/248; 425/143; 156/64, 293, 303.1, 274.4, 322, 309.9, 379.8, 380.9

[56] References Cited

U.S. PATENT DOCUMENTS

| | | | |
|---|---|---|---|
| 4,488,345 | 12/1984 | Müller et al. | 156/303.1 |
| 4,994,132 | 2/1991 | Liekens et al. | 156/303.1 |
| 5,034,082 | 7/1991 | Nolan | 156/293 |
| 5,582,663 | 12/1996 | Matsunaga | 156/64 |

*Primary Examiner*—P. W. Echols
*Attorney, Agent, or Firm*—Lundy and Associates

[57] ABSTRACT

An improved machine for applying surgical implements to handles comprising a fluent actuated power cylinder with a moveable rod having a distal end. A handle holder is secured to the distal end. The handle holder has a handle cavity therein for holding a surgical implement handle. The handle has an implement stud opening extending axially of the machine. An implement holder having a tool cavity therein for holding a surgical implement with a handle stud facing the stud opening on the machine axis is provided. A stud heater and a stud temperature sensor and a control unit are operatively connected together such that when the control unit is actuated, the stud heater will heat the tool handle stud to a predetermined stud temperature sensed by the sensor which activates the power cylinder to force the handle within the handle holder onto the tool stud and to position the tool stud in the opening of the handle whereby the handle is secured to the tool implement in a manner whereby the tool and handle may be autoclaved repetitively without predetermined failing of the handle.

25 Claims, 5 Drawing Sheets

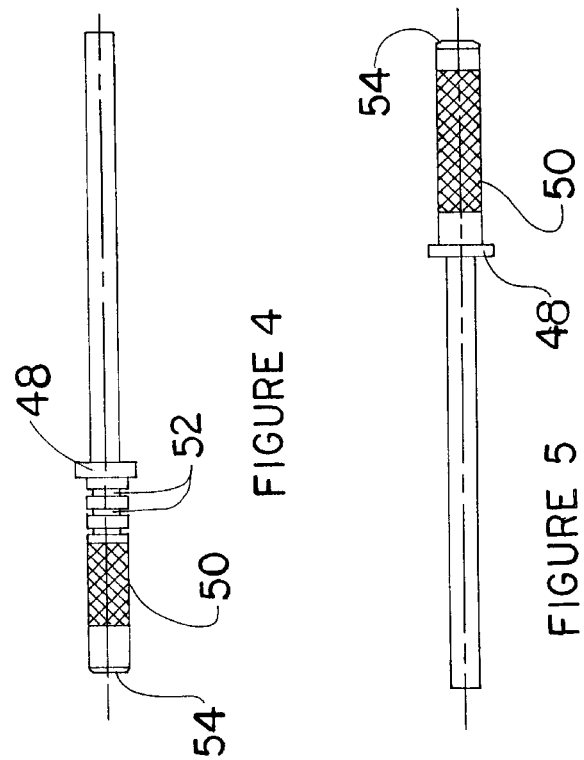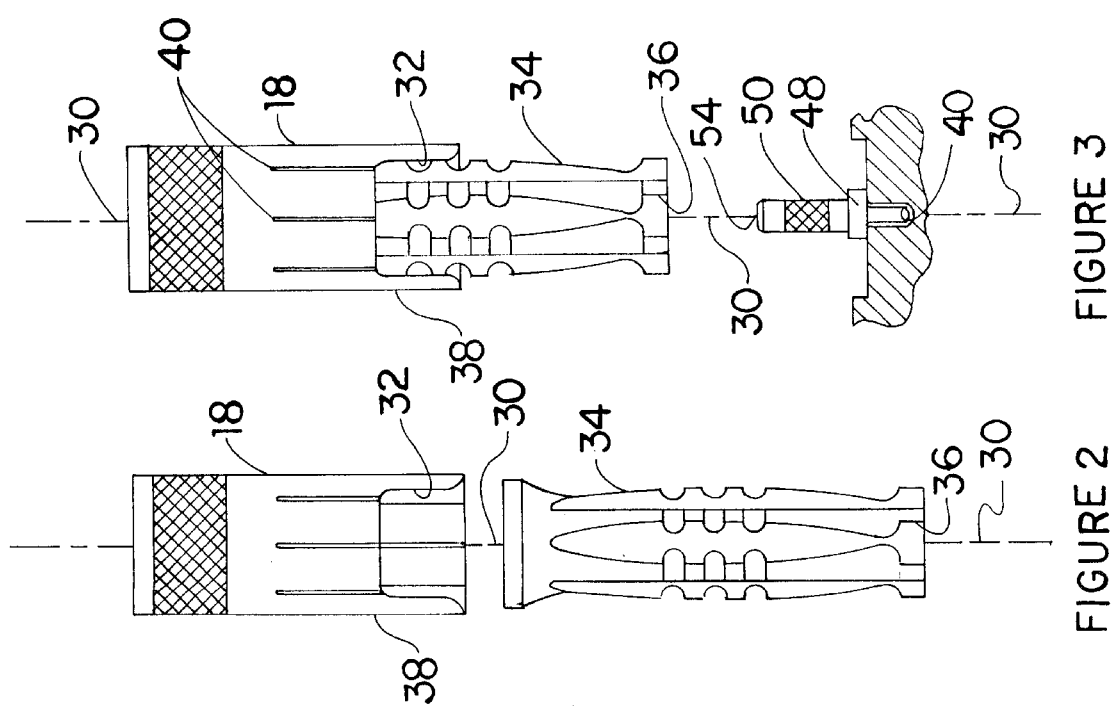

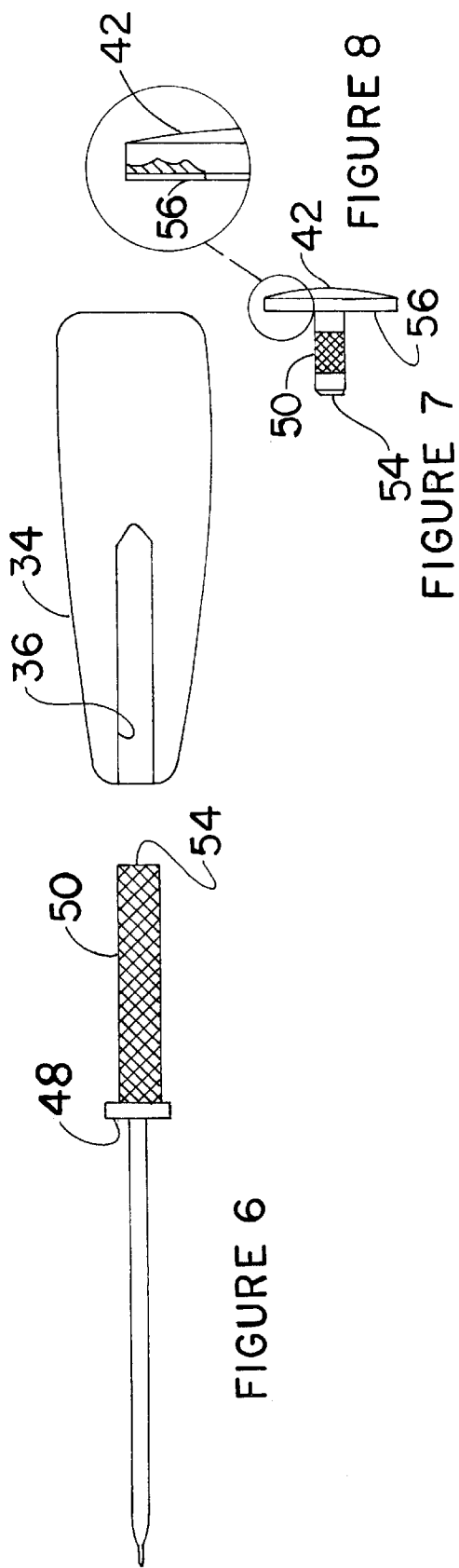
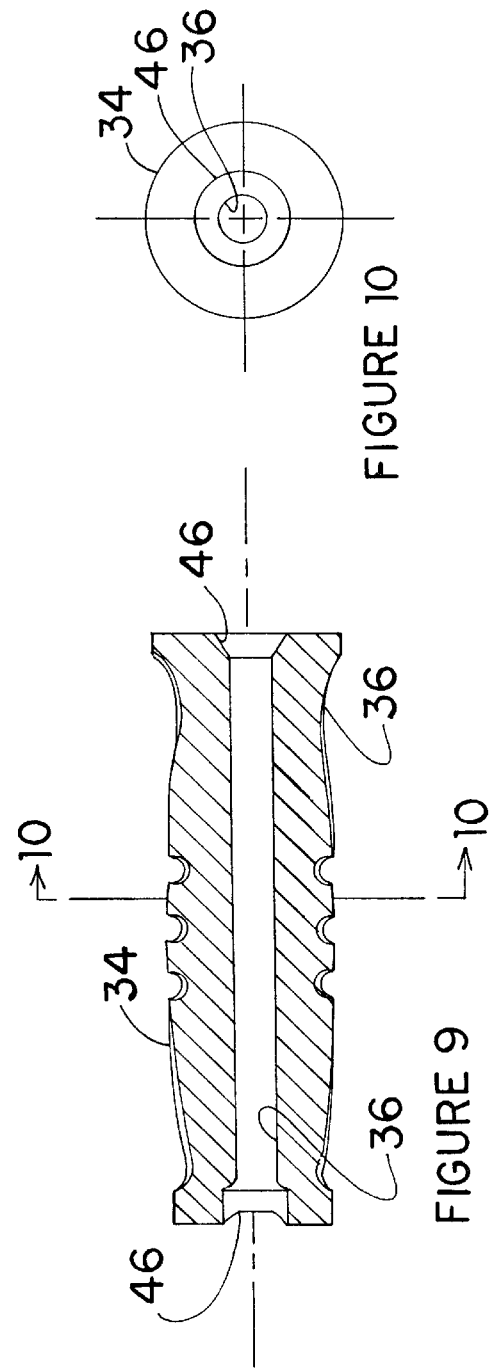

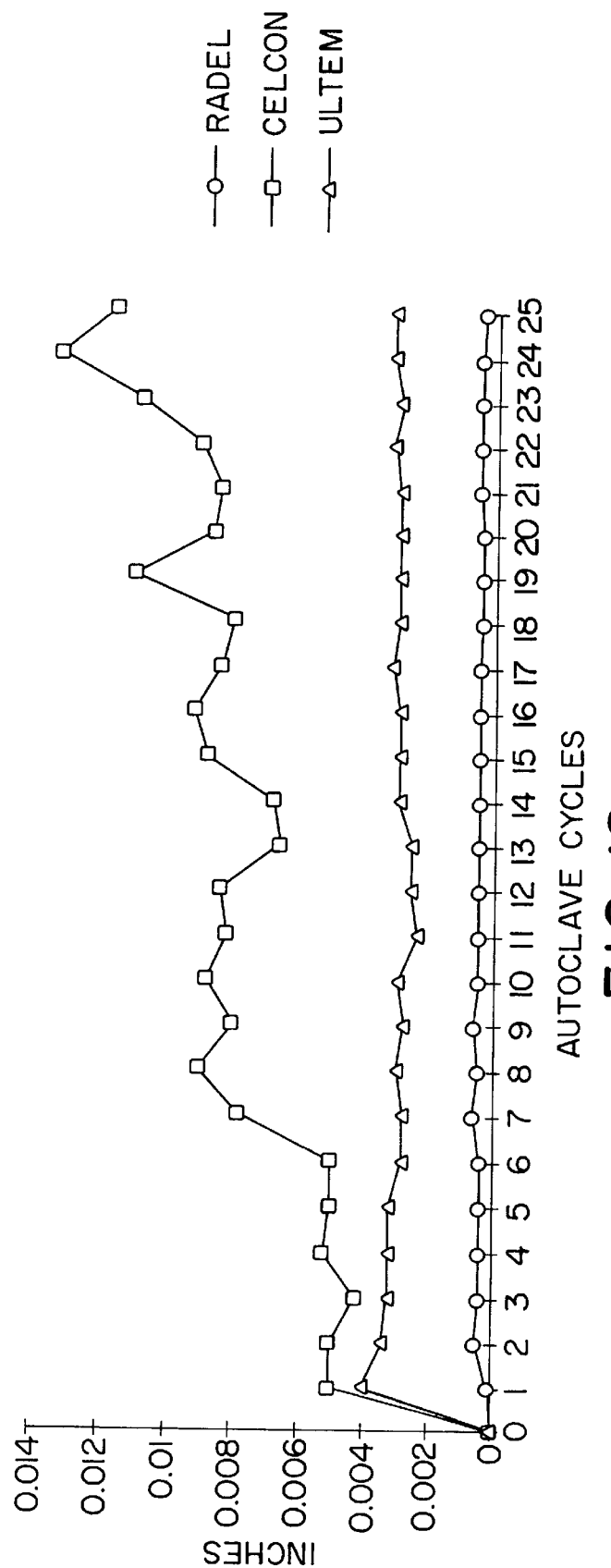

SURGICAL IMPLEMENT HANDLE MACHINE

The present invention relates to a machine for applying surgical implements such as chisels, borers, reamers, screwdrivers, and striking plates to handles therefore; and more particularly, to a surgical implement handle machine which applies handles to surgical implements which may be repetitively autoclaved for sterilization along with the instrument without premature failure.

Surgical instruments with handles have long been used. Surgical implement handles applied to surgical instruments have been fastened by a variety of ways including by adhesives and rivets or pins extending through the handles and the tool. However in the past, surgical implement handles have had a relatively short life due to the repetitive autoclaving necessary to sterilize surgical tools prior to an operation.

Heretofore surgical tool handles have either grazed, chipped, cracked or broken during repetitive autoclaves or have become discolored to make them very unsightly or even nonsterile. It is therefore highly desirable to provide an improved machine for applying surgical implement handles which will result in a tool and handle which can withstand repetitive autoclaving without premature handle failure.

While surgical implement handles of thermoplastic materials have been utilized before, there has been a continuing development with regard to how these handles are applied to surgical implements such that the implements stay secured to the handle and the handles do not prematurely fail due to the repetitive autoclaving cycles of such instruments. After manually assembling handles for some time, it has recently been found that a machine for the assemblage of handles onto surgical implements having a stud forced into a preselected opening of the handle provides surgical implement handles which will survive multiple auto-claves without premature handle failure. It is therefore highly desirable to provide a new and improved automated machine for the securance of thermoplastic handles onto surgical implements having a stud forcefully positioned within an opening in the handle.

It is also highly desirable to provide an improved surgical implement handle which can be assembled repetitively by such a machine within suitable tolerances such that the surgical implements and handles that result will not fail prematurely upon being repetitively autoclaved.

It is also highly desirable to provide an improved machine for reproducibly providing surgical implements with thermoplastic handles which can be repetitively autoclaved without premature failure on command.

Finally it is highly desirable to provide an improved machine for the securance of thermoplastic handles onto surgical implements which possesses all of the above-identified features.

SUMMARY OF THE INVENTION

It is therefore an object of the invention to provide an improved machine for applying surgical implement handles which will result in a tool and handle which can withstand repetitive autoclaving without premature handle failure.

It is also an object of the invention to provide a new and improved automated machine for the securance of thermoplastic handles onto surgical implements having a stud forcefully positioned within an opening in the handle.

It is also an object of the invention to provide an improved surgical implement handle which can be assembled repetitively by such a machine within suitable tolerances such that the surgical implements and handles that result will not fail prematurely upon being repetitively autoclaved can be reproduced.

It is also an object of the invention to provide an improved machine for reproducibly providing surgical implements with thermoplastic handles which can be repetitively autoclaved without premature failure on command.

It is finally an object of the invention to provide an improved machine for the securance of thermoplastic handles onto surgical implements which possesses all of the above-identified features.

In the broader aspects of the invention, there is provided an improved machine for applying surgical implements to handles comprising a fluent actuated power cylinder with a moveable rod having a distal end. A handle holder is secured to the distal end. The handle holder has a handle cavity therein for holding a surgical implement handle. The handle has an implement stud opening extending axially of the machine.

An implement holder having a tool cavity therein for holding a surgical implement with a handle stud facing the stud opening on the machine axis is provided. A stud heater and a stud temperature sensor and a control unit are operatively connected together such that when the control unit is actuated, the stud heater will heat the tool handle stud to a predetermined stud temperature sensed by the sensor which activates the power cylinder to force the handle within the handle holder onto the tool stud and to position the tool stud in the opening of the handle whereby the handle is secured to the tool implement in a manner whereby the tool and handle may be autoclaved repetitively without predetermined failing of the handle.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 2 is an exploded view of the handle holder of the invention and the implement handle to be applied to the surgical implement in accordance with the invention;

FIG. 3 is a fragmentary exploded view of the handle holder with the handle secured thereto with the implement stud positioned in the tool holder in an aligned condition with the handle ready for application;

FIG. 4 is a side view of one surgical implement stud used in the invention;

FIG. 5 is a side view like FIG. 4 of another surgical implement stud used with the invention;

FIG. 6 is an exploded view of yet another surgical implement stud and handle of the invention;

FIG. 7 is a side view like FIG. 4 showing still another surgical implement stud used with the invention;

FIG. 8 is an enlarged side view of a portion of FIG. 7 showing the cap detail of an end cap of the invention;

FIG. 9 is a cross sectional view of one of the handles of the invention taken essentially along the section line 9—9 of FIG. 2;

FIG. 10 is an end view of the handle shown in FIG. 9;

FIG. 12 is a chart showing the change in overall length of the surgical instrument with the handle of the three preferred thermoplastic materials of the invention upon repetitive autoclaving cycles.

DESCRIPTION OF A SPECIFIC EMBODIMENT

Figure 1:
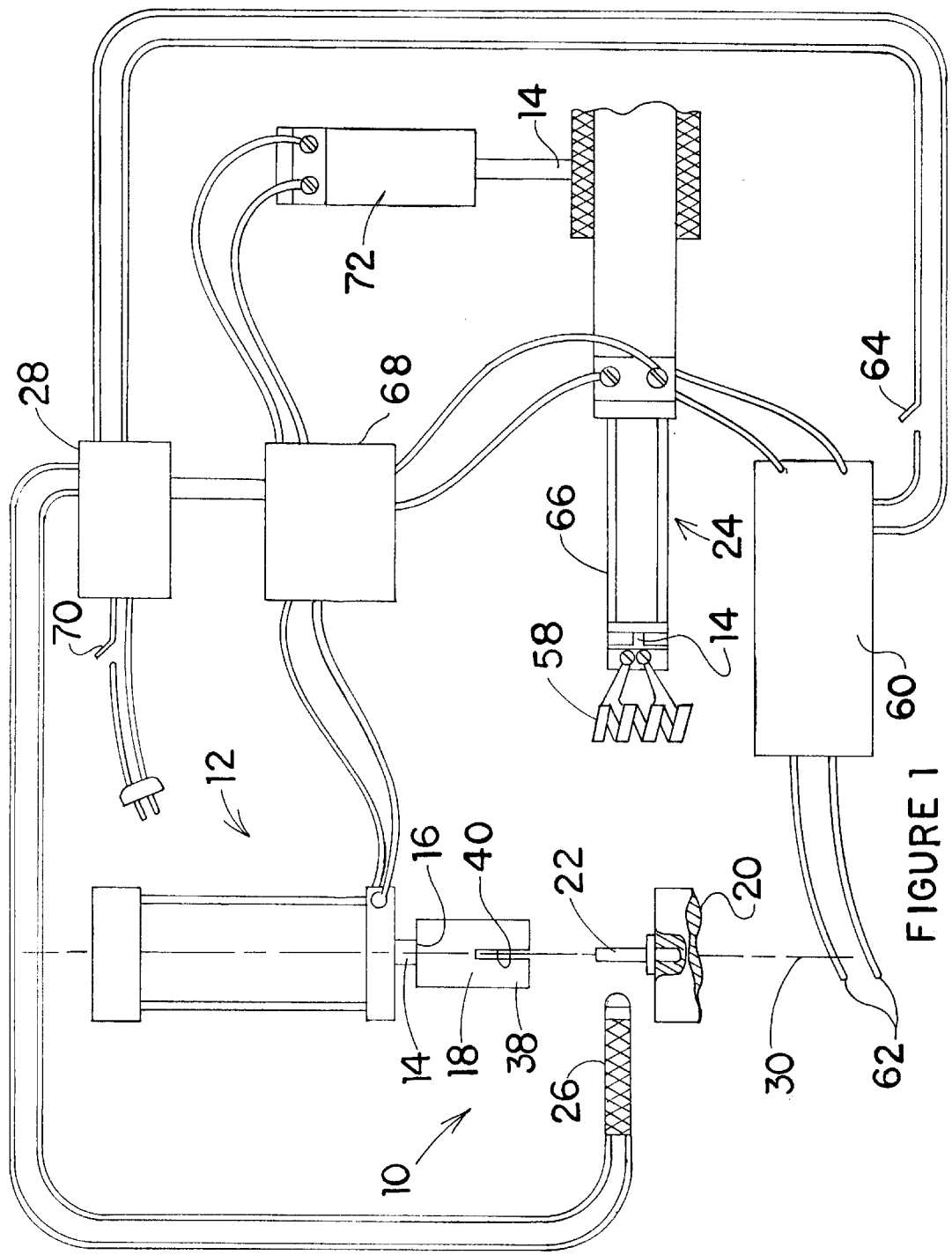
FIG. 1 is a fragmentary diagrammatic view of all of the components of the machine of the invention.
Figure 11:
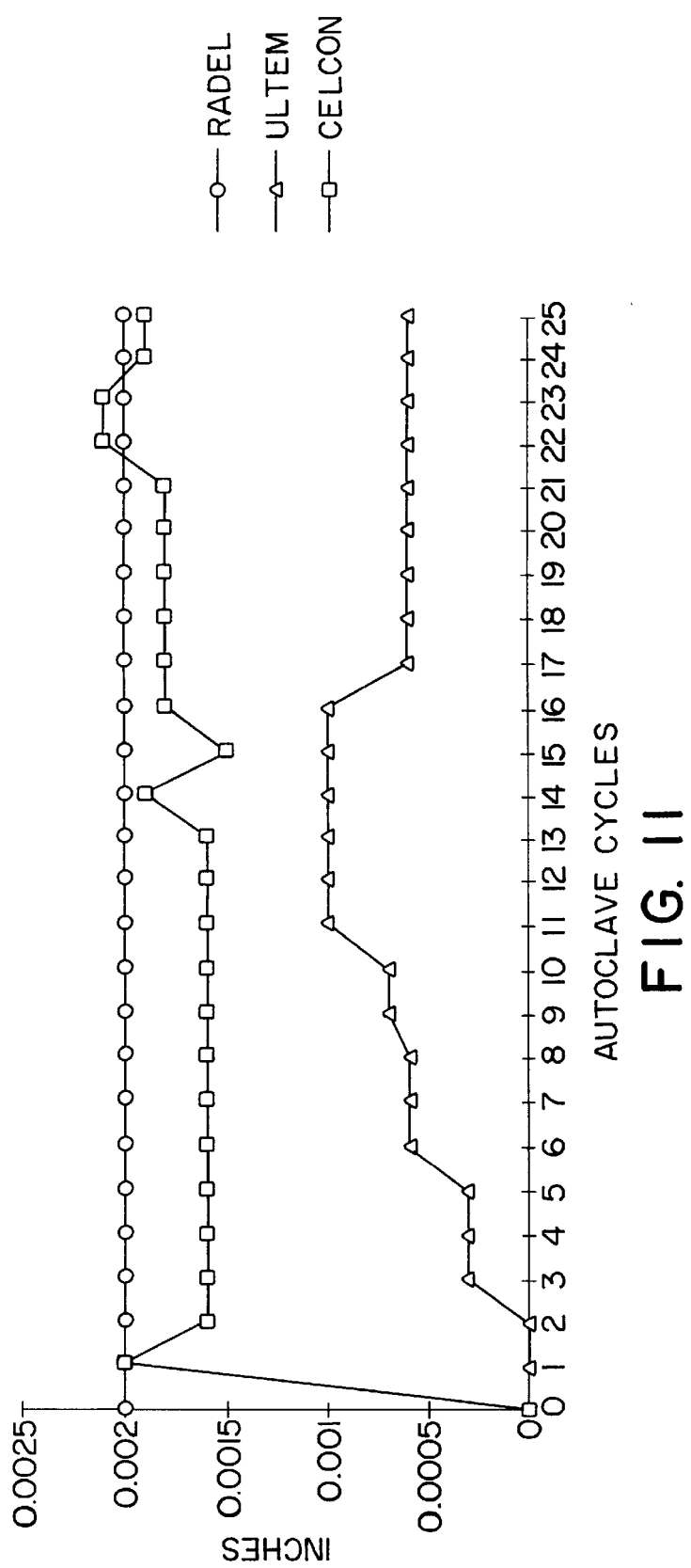
FIG. 11 is a chart showing the change in inches of the striker end gap of handles made of three of the preferred handle materials of the invention upon repetitive autoclaving cycles.

Referring to FIGS. 1 and 2, machine 10 for applying surgical implements to handles is shown to have a fluid cylinder 12 with a moveable rod 14. Rod 14 has a distal end 16 on which a handle holder 18 is secured. An implement holder 20 is aligned with the handle holder to hold implement handle stud 22 which will be described in detail hereinafter. A stud heater 24 is provided to heat the handle stud 22 as desired. A stud temperature sensor 26 is provided to sense the temperature of the stud 22. A control unit 28 is operatively connected to the fluid cylinder 12, the stud heater 24 and the stud temperature sensor 26 such that when the control unit 28 is actuated, the stud heater 24 is turned on until the stud 22 is heated to a predetermined stud temperature sensed by the sensor 26 at which time the control unit 28 actuates the fluid cylinder 12 as will be described hereinafter.

Fluid cylinder 12 may be a pneumatic or hydraulic cylinder having a rod 14 which is moveable from about 4 to about 8 inches. Fluid cylinder 12 is shown mounted with its rod 14 defining a vertical axis 30 of the machine. In another specific embodiment, vertical axis 30 may be generally horizontal or at other attitudes as desired.

Handle holder 18 has a handle cavity 32 for holding a surgical implement handle 34. Handle 34 has an implement stud opening 36 therein. Handle cavity 32, handle 34 and handle stud opening 36 each have axes which when handle 34 is positioned within handle holder 18 are coincident with axis 30. In the specific embodiment illustrated in FIGS. 1–3, handle holder 18 is a split collet 38 by which handle 34 is secured by the frictional grasp of the collet 38 as it expands to hold the handle 34 rigid and coaxial with axis 30. Handle 34 as shown in FIGS. 2 and 9, is designed such that both ends are generally identical such that the handle 34 may be reversed within the collet 38 as desired, as will be explained in detail hereinafter. Handle 34 as shown in FIG. 6 is not reversible.

In a specific embodiment, handle cavity 32 is about 1.30 inches plus or minus 0.01 inch in diameter for use with a handle which has an outside diameter of about 1.60 inches plus or minus 0.01 inch. Handle cavity 32 is from about 2 to about 4 inches long in order to hold the handle 34 securely, rigidly in position.

In a specific embodiment, the handle holder 18 is in the form of split collet 38 with an inside diameter of about 1.60 inches plus or minus 0.01 inch and has evenly positioned around its periphery six slots 40 extending axially from about 1 to about 1.25 inches long.

Handle 34 may have an implement stud opening 36 at one end as shown in FIG. 6 or have an implement stud opening 36 at both of its opposite ends as shown in FIG. 9. Each of the stud openings 36, in all specific embodiments, are adapted to receive the stud 22 of a surgical implement. One example of a surgical implement requiring stud openings 36 at the opposite ends of the handle 34 is a chisel which at one end of the handle 34 the chisel is secured to the handle 34 by one stud opening 36 and at the other end of the handle 34 a striker plate 42 is secured to the handle 34 by the other stud opening 36. An example of a handle 34 having only a single stud opening 36 would be that of a screw driver. In specific embodiments, the stud opening 36 is about the same size as the implement stud 22 as will be mentioned hereinafter.

Tool or implement holder 20 is provided to hold the implement stud 22 on which the surgical handles 34 are to be applied by the machine 10. Tool holder 20 in a specific embodiment is a conventional three jaw chuck mounted with its axis coincident with machine axis 30. Tool holder or chuck 20 has a tool receiving cavity 44 which has an axis coincident with machine axis 30 and is rigidly fixed with respect to handle holder 18.

Each tool held by tool holder 20 has a tool stud 22 with an axis which when held by tool holder 20 positions stud 22 with its axis coincident with machine axis 30 extending away from the tool holder 20 toward the handle holder 18.

Surgical implement or tool studs 22 in all specific embodiments are generally about the same size as the stud opening 36 in handle 34 with an enlarged knurl section 50 which provides an interference fit between tool stud 22 and handle opening 36. In a specific embodiment stud, opening 36 is 0.376 plus or minus 0.005 inches in diameter and is equipped with an entry bevel 46 at an approximate angle of 45° with axis 30 and an entry bevel periphery of 0.395 plus or minus 0.001 inches. Tool stud 22 used with the above specific embodiments of stud opening 36 is from about 0.375 plus or minus 0.002 inches in diameter with a heavy knurl section 50 of about 0.400 inches plus or minus 0.001 inches in diameter extending axially along the stud. In a specific embodiment, the stud has a collar 48 spaced from the knurl section 50 of the stud 22 and several generally rectangular grooves 52 encircling the stud of about 0.050 inches in axial length spaced apart 0.125 inches. The knurl section 50 extends axially from about 0.75 to about 1.13 inches and the entire tool stud is about 1.5 inches to about 2.5 inches in axial length between collar 48 and its distal end 54.

In such an embodiment, handle stud opening 36 is approximately 2.5 inches long. The handle is approximately 5 inches in axial length.

Striker cap 42 is provided with a similar stud 22; however the striker cap 42 is provided with a peripheral upstanding edge 56 of about plus or minus 0.02 inches which embeds itself into the handle adjacent the handle diametral periphery.

Implement handles 34 are each made of a thermoplastic resin having a softening point, melting point, and/or glass transition temperature from about 329° to about 450°, an izod on impact strength of about 1.0 to about 1.5, an elongation at break point greater than 30 and a tensile strength from about 12,000 to 18,000. In a specific embodiment, suitable handles 34 can be manufactured from RADEL polyphenyl sulfone, RADEL polyether sulfone, CELCON ACETAL and ULTEM polyetherimide resins. CELCON ACETAL can be purchased from West Lake Plastics Company of Lenni, Pa., ULTEM polyetherimide resin may be purchased from West Lake Plastics Company of Lenni, Pa., and RADEL polyphenyl sulfone and polyether sulfone resins can be purchased from Amoco Performance Products Inc. of Ridgefield, Conn. or Marion, Ohio.

Referring now to FIG. 1, there is shown the control unit 28 connected in a schematic diagram to stud heater 24 and the stud temperature sensor 26 together with the operator 68 of the cylinders 12, 66 and 72. In a specific embodiment, control unit 28 is a PC controller which includes RAM memory, supply inputs and outputs and capabilities of expansion modules. In a specific embodiment, the control unit is a D100 PC controller as manufactured by ETN's Cutler Hammer Division.

Control unit 28 is interconnected with the stud temperature sensor 26 which in a specific embodiment is an infrared temperature sensor located adjacent surgical implement stud 22 when stud 22 is held fast by the implement holder 20. Control unit 28 is also operatively connected to the stud heater 24 which in a specific embodiment is an induction heater having a heating coil 58 which at least partially surrounds stud 22 when in a heating position. The heating coil 58 is connected to a fluid cylinder 66. Fluid cylinder 72 is connected to cylinder 66 to move heating coil 58 and cylinder 66 as a unit generally axially of machine 10 and generally perpendicularly of the direction of motion of cylinder 66 to position heating coil 58 particularly around stud 22. Cylinder 72 is operated by operator 68 along with the fluid cylinders 12 and 66. Operator 68 includes fluid valving which is operatively connected to the control unit 28 as shown.

Tool stud heater 24 includes a water cooled power supply 60 which is connected to local water taps 62 and is fixed in position in contrast to the heating coil 58 which is moveable both with fluid cylinder 66 and independently of fluid cylinder 66 by fluid cylinder 72.

In a specific embodiment, the induction heater 24 and power supply 60 may be a Magniforce Model 5E3 induction heating system.

Cylinders 12, 66 and 72 each have adjustments thereon whereby the extension of rods 14 of each can be adjusted between stops. As will be mentioned hereinafter, these stops need to be adjusted when the surgical implement to which the handles 34 are to be attached by machine 10 or the handles 34 themselves, are changed from handles of one type or dimension to another type or dimension.

Included in FIG. 1 is a power on/off switch 70 for the control unit 28 and a power on/off switch 64 for the induction heater 24. Control unit 28 times out the actuation of the fluid cylinders 12, 66, 72 and induction heater 24 in accordance with the operation of the machine 10 which will now be described.

In operation, a surgical implement to be attached to the handle 34 is fixed in the implement holder 20 with its implement stud 22 extending axially of machine 10. A surgical implement handle 34 is inserted into the handle opening 32 of the handle holder 18. In the specific embodiment in which the handle holder 18 is a split collet 38, the handle 34 is inserted into the collet 38 forcibly to spread the collet 38 and to rigidly hold the handle 34 in the collet 38 by friction with the stud hole 36 of the handle 34 extending coaxially of machine axis 30. In the specific embodiment illustrated, handle 34 is inserted when the rod 14 of the fluid cylinder 12 is fully retracted. In this position, handle 34 and implement stud 22 are positioned on axis 30 in a spaced apart fashion.

The stops on fluid cylinders 12, 66 and 72 need to be adjusted so that when the rods 14 thereof are fully extended, the handle 34 within the collet 38 will be extended to the collar 48 of the tool stud 22 and the heating coil 58 will be extended and properly positioned to partially surround tool stud 22, respectively, when cylinders 66 and 72 are extended.

Control unit 28 is then actuated by throwing off/on switch 64 and 70 to an "on" position. Control unit 28 actuates fluid cylinder 72 to position heating coil 58 in registry with tool stud 22, actuates fluid cylinder 66 to extend its rod 14 to its maximum extension to position heating coil 58 about implement stud 22, and turns on stud heater 24. Stud heater 24 heats the implement stud 22 to a temperature approximately 100° F. hotter than the handle application temperature. In a specific embodiment in which handle materials are chosen form polyether and polyphenol sulfones, acetals and polyetherimides, the stud heater 24 is set to heat the implement stud 22 to a temperature from about 625° to about 675°. When the stud 22 reaches this temperature as sensed by the stud temperature sensor 26, the stud temperature sensor 26 signals the control unit 28 and the control unit 28 signals the cylinder operator 68 to withdraw the rod 14 of cylinder 66 and thereby move the heating coil 58 of the stud heater 24 away from the heated stud 22 clearing the space between the implement handle 34 within the handle holder 18 and the stud 22 within the tool holder 20.

Control unit 28 then actuates fluid cylinder 12 to extend its rod 14, handle holder 18 and the handle 34 therein to its full extent as adjusted. The movement of rod 14 first engages handle 34 with the stud 22, heated stud 22 is then forced into the stud hole 36 of the handle 34. Stud 22 heats the material of the handle 34 surrounding hole 36. The material of the handle 34 flows around the heated stud 22 into grooves 52 and knurl section 50. When rod 14 of cylinder 12 is fully extended, it is held there under pressure for a predetermined time. In a specific embodiment, cylinder 12 holds the rod 14, handle 34 and stud 22 together under pressure from about 45 seconds to about 90 seconds.

The implement holder 20 is then released and the rod 14 of cylinder 12 is retracted. The surgical implement with handle 34 attached is then removed from the handle holder 18 and the machine is reloaded with another surgical implement with stud 22 and handle 34.

By operating the machine repetitively, handles may be applied to surgical implements in an improved manner. Handles applied to surgical instruments by the machine result in a tool and handle which can withstand repetitive autoclaving without premature handle failure. By applying the handles to surgical implements by the machine, thermoplastic handles are applied to surgical implements in a manner which repetitively produces surgical implements and handles that will not prematurely fail upon being repetitively autoclaved.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A machine for applying surgical implements to handles comprising a fluid actuated power cylinder, said cylinder having a moveable rod, said rod having a distal end, a handle holder secured to said distal end, said handle holder having a handle cavity therein for holding a surgical implement handle having an implement stud opening therein, an implement holder having an implement cavity therein for holding a surgical implement with a handle stud facing said stud opening, said stud opening and said handle stud being on the same axis, a stud heater, a stud temperature sensor, and a control unit, said control unit being operatively connected to said cylinder and said heater and said sensor, said control unit upon command turning said stud heater on until said stud is heated to a predetermined stud temperature sensed by said sensor, and then activating said cylinder to force said stud into said stud opening of said handle, thereby securing said handle to said stud implement.

2. The machine of claim 1 wherein said stud heater is an induction heating coil, said coil in a heating position at least partially surrounding said stud.

3. The machine of claim 2 further comprising a fluid actuated cylinder, said cylinder having a moveable rod with a distal end, said heating coil being secured to said distal end, whereby said heating coil is moveable into and out of said heating position.

4. The machine of claim 3 wherein said power cylinder is a pneumatic cylinder.

5. The machine of claim 3 wherein said cylinder rod moves from about 4 to about 8 inches.

6. The machine of claim 1 wherein said temperature sensor is an infrared sensor.

7. The machine of claim 1 wherein said power cylinder is a pneumatic cylinder.

8. The machine of claim 1 wherein said cylinder rod moves from about 4 to about 8 inches.

9. The machine of claim 1 wherein said handle holder is a split collet, said handle cavity therein being from about equal but smaller than to about ½ inch smaller than the handle to be held in said cavity by said collet.

10. The machine of claim 9 wherein said collet handle cavity which is from about 0.2 to about 0.4 inches smaller in diameter than the diametral size of the handle to be held in the collet and from about ⅓ to about ¾ of the length of said handle.

11. The machine of claim 10 wherein said collet has a plurality of slots circumferentially equally spaced around said collet.

12. The machine of claim 1 wherein said implement holder is a conventional three jaw chuck.

13. The machine of claim 1 wherein said axis extends generally vertically.

14. The machine of claim 1 wherein said stud opening of said handle is from about 0.01 to about 0.02 inches smaller than said implement handle stud.

15. The machine of claim 14 wherein said stud opening is 0.376 inches plus or minus 0.005 inches in diameter, said stud opening has a entry bevel from about 43° to about 47° with said axis, and wherein said implement handle stud has a knurled portion thereon of about 1 to about 2 and ½ inches in axial length.

16. The machine of claim 15 wherein said knurled portion is a 21 pitch knurl from about 0.3 to about 0.5 inches in depth.

17. The machine of claim 15 wherein said implement stud has at least one groove therein adjacent said knurled portion extending radially inwardly thereof.

18. The machine of claim 1 wherein said surgical implement stud is chosen from the group consisting of handle studs of striker caps, chisels, reamers, tool drivers, and hammers.

19. The machine of claim 1 wherein said stud heater is an induction heater having the capability of heating said stud to a temperature of about 100° F. above the melting point of the material of said handle.

20. The machine of claim 1 wherein said handles are chosen from implement handles made from handle materials of the group consisting of polyether sulfones, polyphenol sulfones, acetals and polyetherimides and combinations thereof having softening points and melting points and glass transition temperatures from about 300° F. to about 500° F. and elongations at break points greater than about 30%.

21. The machine of claim 20 wherein said stud opening of said handle is from about 0.01 to about 0.02 inches smaller than said implement handle stud.

22. The machine of claim 21 wherein said stud opening is 0.376 inches plus or minus 0.005 inches in diameter, said stud opening has an entry bevel from about 43° to about 47° with said axis, and wherein said implement handle stud has a knurled portion thereon of about 1 to about 2 and ½ inches in axial length.

23. The machine of claim 22 wherein said surgical implement stud is chosen from the group consisting of handle studs of striker caps, chisels, reamers, tool drivers, and hammers.

24. The machine of claim 21 wherein said knurled portion is a 21 pitch knurl from about 0.3 to about 0.5 inches in depth.

25. The machine of claim 21 wherein said implement stud has at least one groove therein adjacent said knurled portion extending radially inwardly thereof.

\* \* \* \* \*